އ73-631

XR  4,043,181

United States Patent [19]
Nigam

[11] 4,043,181
[45] Aug. 23, 1977

[54] ULTRASONIC PULSE-ECHO APPARATUS
[75] Inventor: Anant K. Nigam, Fairfield, Conn.
[73] Assignee: New York Institute of Technology, Old Westbury, N.Y.
[21] Appl. No.: 569,185
[22] Filed: Apr. 18, 1975
[51] Int. Cl.² ........................................... G01N 29/00
[52] U.S. Cl. ............................................... 73/67.8 R
[58] Field of Search ............... 73/67.8 R, 67.8 S, 67.9, 73/71.5 US, 67.5 R, 67.7; 128/2 V, 2.05 Z

[56] References Cited
U.S. PATENT DOCUMENTS

| 3,033,029 | 5/1962 | Weighart | 73/67.8 R |
|---|---|---|---|
| 3,287,962 | 11/1966 | Relyea et al. | 73/67.9 |
| 3,348,410 | 10/1967 | Henry | 73/67.8 R |
| 3,367,173 | 2/1968 | Uphoff | 73/67.8 R |
| 3,552,191 | 1/1971 | Heseding | 73/67.7 |
| 3,608,361 | 9/1971 | Krautkramer | 73/67.7 |
| 3,690,153 | 9/1972 | Matay | 73/67.8 R |
| 3,778,757 | 12/1973 | Houston | 73/67.7 |

Primary Examiner—Richard C. Queisser
Assistant Examiner—Stephen A. Kreitman
Attorney, Agent, or Firm—Martin Novack

[57] ABSTRACT

For use in ultrasonic pulse-echo apparatus including an ultrasonic wave transducer for transmitting an ultrasonic wave toward an object to be examined and for producing an electric signal corresponding to echo pulses reflected by the object, an improved signal processing circuit for compensating for attenuation effects caused by ultrasound absorption, diffraction, reflection and scattering. Compensation for these image-degrading effects assures simple, reliable and repeatable equipment performance, and contributes to reliable detection of very weak echoes.

14 Claims, 8 Drawing Figures

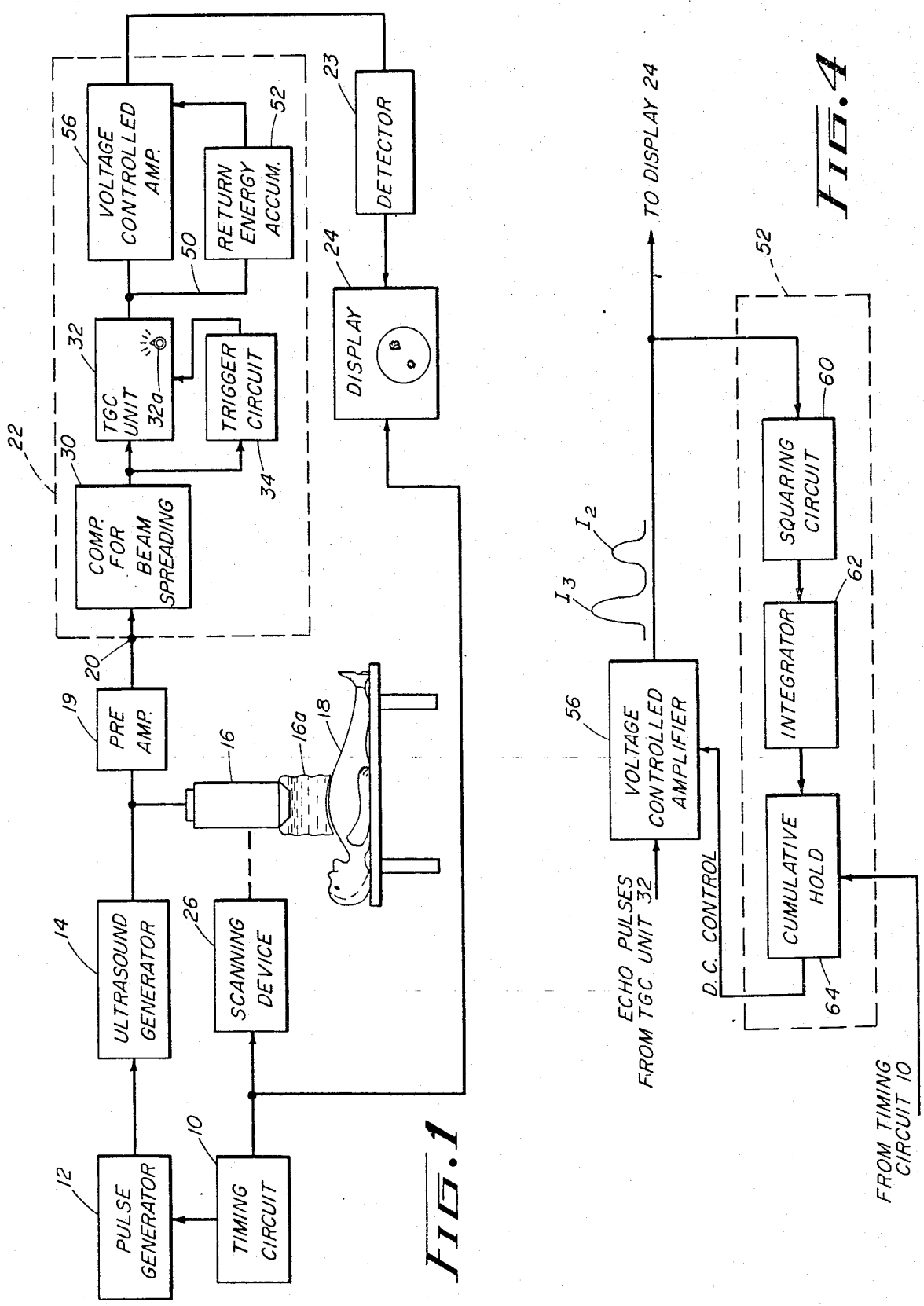

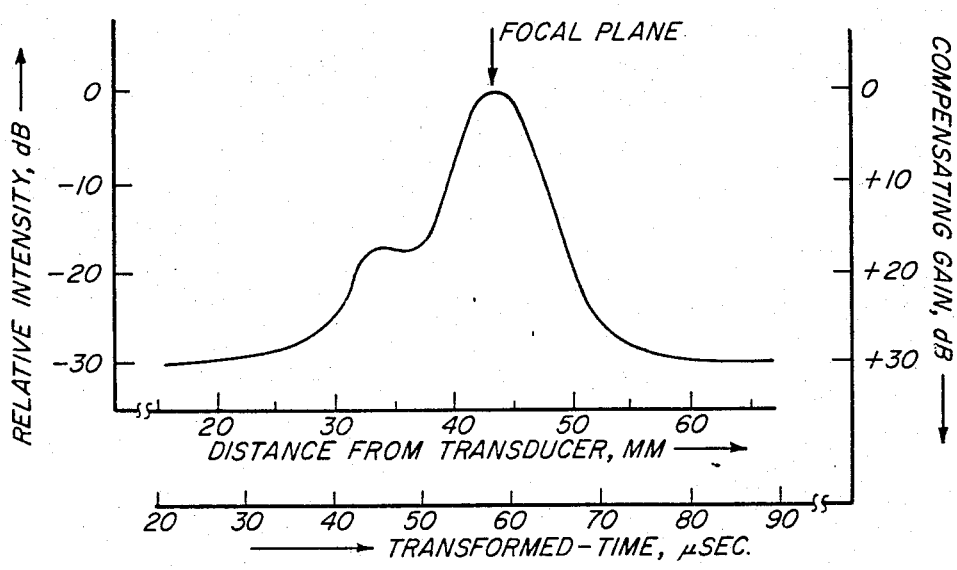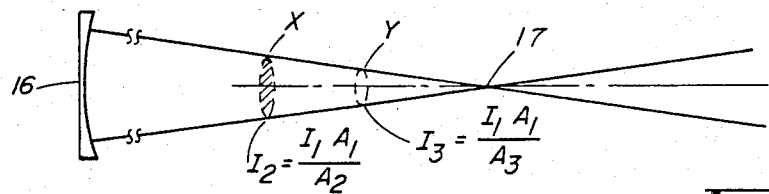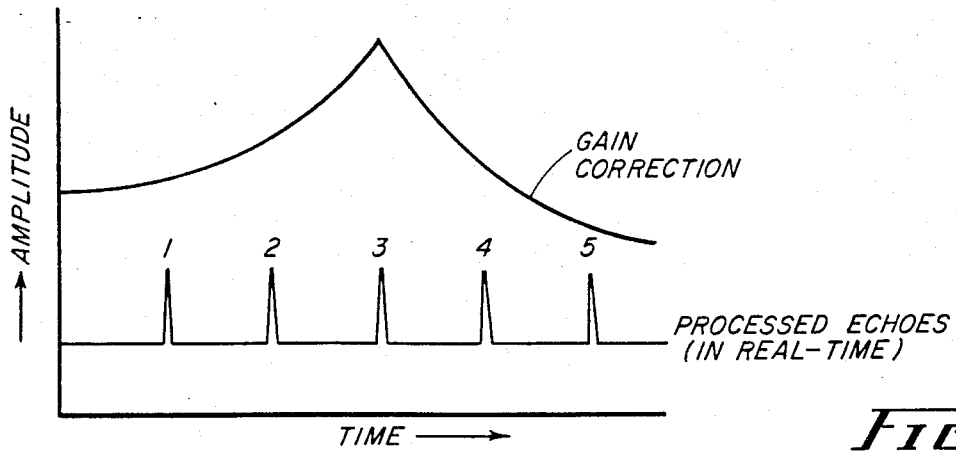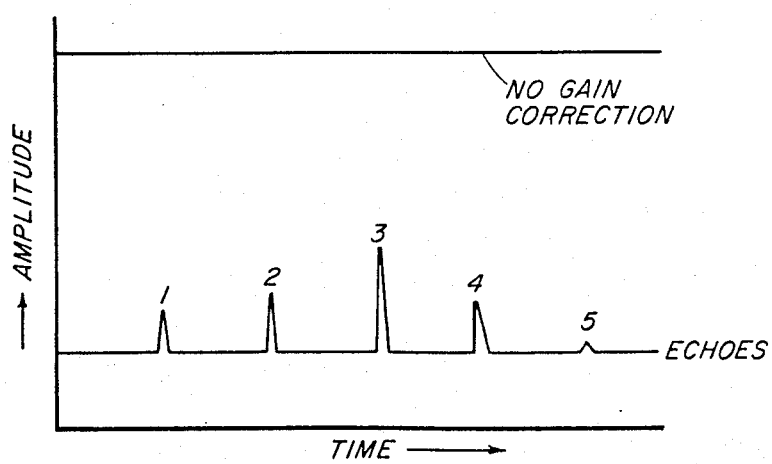

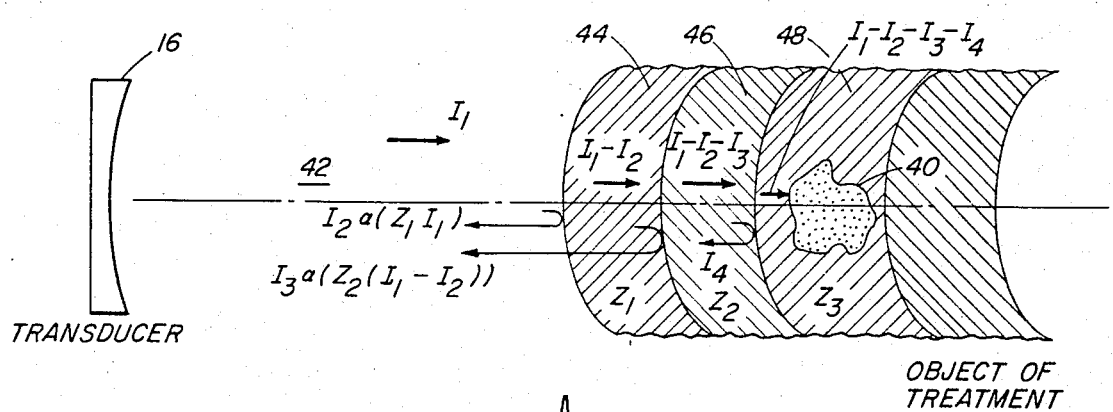
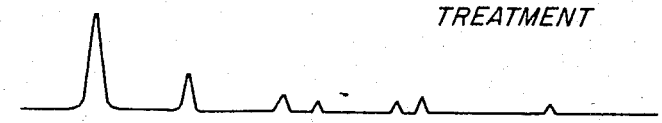
FIG.3
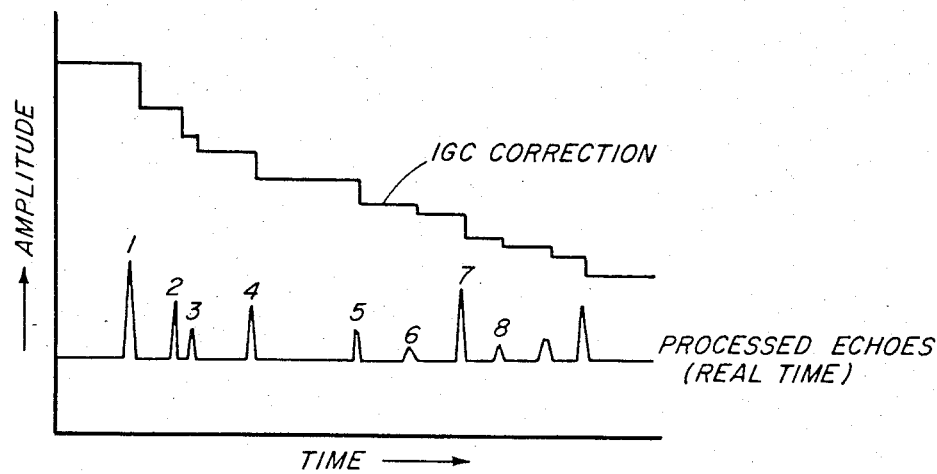
FIG.5
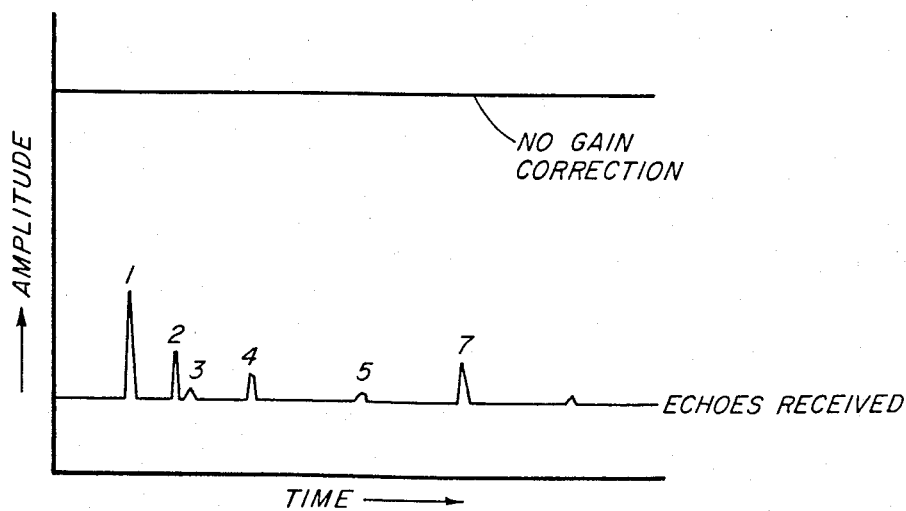
FIG.6

ULTRASONIC PULSE-ECHO APPARATUS

BACKGROUND OF THE INVENTION

Ultrasound pulse-echo apparatus is known and available for non-invasive imaging of humans and animals in studying the internal anatomy, as well as for nondestructive testing of engineering materials for flaws, inclusions, cracks or fissures. In such systems, a series of very short ultrasound pulses are transmitted through a suitable conducting medium (usually water) to the object under test. The returning echoes from increasing depths in the object arrive at the receiver at successively increasing time delays with respect to the time of pulse initiation. These echoes are displayed on a cathode-ray tube (CRT) in an A-, B-, or C-scan presentation as the ultrasound beam is scanned over the object to produce a television-type image of the interior of the object. The amplitude or strength of the echoes is displayed as a corresponding brightness level of the image; viz, a strongly reflecting internal structure, such as hardened artery walls, appear brighter on the display than more weakly reflecting structures. This relative brightness or gray scale in the display serves as a useful tool in the diagnosis of the flaw or diseased organ, as the case may be.

In such ultrasonic imaging systems, as the object is being interrogated by the unltrasound beam it produces a set of ultrasound echoes which represent in real-time the various acoustical interfaces within the object. The amplitude of such echoes is proportional to both the intensity of the transmitted ultrasound pulse and the mechanical impedance discontinuity at the interface, while the time-spacing between the echoes is proportional to the physical spacing of the respective reflecting interfaces. In general, the object medium absorbs ultrasound energy (which is converted within the object to heat) and consequently the echoes from increasing depth in the object are imaged by gradually diminishing incident ultrasound energy, resulting in decreasing echo strengths from deeper lying structures. It is known in the prior art to offset the above-described effects due to absorption in the object medium by increasing, monotonically with time, the electronic gain of the signal processing circuit which couples the electrical signals from the transducer to the display. This is known as time-again compensation (TGC) and is arranged to provide successively higher gain to echoes arriving later in time; that is, from increasing depths in the object in an attempt to compensate for the absorption effects.

It has been found, however, that mechanisms other than absorption effect exist which attenuate the ultrasound pulse as it progresses deeper within the object The present invention is based on the recognition of these additional effects and how they can be compensated to improve the performance of ultrasound apparatus.

The ultrasound absorption properties of object media are generally given by $$I = I_o e^{-\alpha z} = I_o e^{-(\alpha/c)t} \qquad \text{Eq. (1)}$$

where I is the intensity of the ultrasound pulse, z is the propagation path-length, $\alpha$ and c are the attenuation coefficient and ultrasound velocity in the medium, respectively, and t is the arrival time at the transducer of the reflected pulse. Thus, the correction for object medium absorption effects is simply a time-gain compensation of the form $e^{+(\alpha/c)t}$. In addition to absorption there are various other attenuation mechanisms, particularly the geometrical damping mechanisms associated with beam spreading and/or focussing, and reduction in the incident ultrasound intensity at successive interfaces due to reflection and scatter at the preceding interfaces and/or media. In an attempt to take these other effects into account, TGC circuits have heretofore been modified, as by operator-controlled adjustment of certain parameters of the TGC circuit, to provide arbitrarily-shaped timegain characteristics. The extreme flexibility introduced by the operator control of the TGC circuit, however, not only subjects the equipment operator to a baffling array of knobs and controls, but gives rise to the much more fundamental problem of lack of repeatability of the image insofar as the operator cannot reproduce the complex time-gain function with any exactness at a later point in time.

It is a primary object of the present invention to provide an improved ultrasonic pulse-echo apparatus capable of providing compensation for all three of the major attenuation effects outlined above with a view toward simplification of the apparatus from the operator's point of view, and improvement in echo detection and repeatability of the diagnostic results over that obtainable with pulse-echo apparatus heretofore available.

SUMMARY OF THE INVENTION

These and further objects are accomplished by providing in ultrasonic pulse-echo apparatus of the type including a transducer for directing a beam of ultrasound pulses toward an object to be examined and for converting the ultrasound echo pulses reflected from within the object to electrical pulses, and television-type display means responsive to the electrical pulses for displaying the image of the object, signal-processing means connected between the transducer and the display means operative to vary the gain of the pulses in a manner to compensate for the major attenuation effects within the object medium. Corrections for attenuation of the ultrasound beam due to reflections within the object are provided by means responsive to the electrical signals from the transducer for varying the gain interactively, in real-time, to provide a gain value which at any instant of time following transmission of each ultrasound pulse is proportional to the cumulative energies of the echo pulses received by the transducer up to said instant of time. Correction for effects of absorption of the ultrasound beam in the object is provided by means for varying the gain in accordance with a predetermined time-gain function, the shape of which is selectable according to the absorption coefficient of the object being examined. Corrections for spreading and/or focussing effects of the ultrasound beam are provided by means in the signal-processing circuit for varying the gain in accordance with another predetermined time-gain function the shape of which depends on the characteristics of the beam produced by the transducer employed in the apparatus.

BRIEF DESCRIPTION OF THE DRAWINGS

A better understanding of the invention will be had from the following detailed description, taken in conjunction with the accompanying drawings, in which:

FIG. 1 is a block diagram of ultrasonic pulse-echo apparatus embodying the invention, showing its use in imaging of the human body;

FIG. 2 is a diagram illustrating the attenuation due to the on-axis intensity distribution of the ultrasound beam from the transducer and the time-gain function for compensating therefor;

FIGS. 2A and 2B illustrate typical A-scans showing the effect of correction for "beam spreading" losses;

FIG. 3 is a diagram illustrating the attenuation caused by reflections as the ultrasound pulse propagates across a series of interfaces;

FIG. 4 is a block diagram of a preferred embodiment of an interactive gain compensation circuit for providing corrections for attenuation due to reflections within the object;

FIG. 5 is a typical A-scan (single line of the image field) made with the reflection compensation circuit of FIG. 4 operating; and FIG. 6 illustrates the same signal as is shown in FIG. 5 with the circuit of FIG. 4 disconnected.

DESCRIPTION OF THE PREFERRED EMBODIMENTS

Referring to FIG. 1, which illutrates in block diagram form those components of an ultrasonic diagnostic system necessary for an understanding of the present invention, a trigger signal produced by a timing circuit 10 is coupled to a pulse generator 12 which produces a pulse signal which is applied to an ultrasound generator 14 which produces an ultrasonic pulse of suitable center frequency, frequencies in the range of 1MHz and 10MHz being typical. The ultrasound pulses produced by generator 14 are applied to an ultrasound wave transducer 16 shown, by way of example, in the form of a probe, which radiates the sound energy toward the object to be imaged, in this example, a patient 18. The ultrasonic energy reflected by the patient 18 is received again by the transducer 16 and converted into an electric signal, which is amplified by a pre-amplifier 19 and applied to the input terminal 20 of signal-processing circuitry 22. The output from the signal-processing circuit 22, the operation of the components of which will be described hereinbelow, is detected by a detector 23 to produce an image signal for presentation on a suitable display 24, which may be of any known type, e.g. either an A-scan, B-scan or C-scan. The transducer 16 is mechanically (or by other means) interlocked with a scanning device 26 for moving the transducer, if desired, at a definite rate and in a predetermined direction across the surface of the patient 18. Movement of the scanning device and the operation of the display, which conventionally takes the form of a cathode ray tube, are synchronized by signals from timing circuit 10 to produce a television-type display.

In order for the described system to provide meaningful diagnostic data, it first must be capable of detecting the volume to be investigated, such as, for example, an internal organ, and secondly, the displayed results should be repeatable. Among the problems faced in detection is that a strong reflector of ultrasonic energy may be present between the transducer and the volume to be investigated; in the ultrasonic imaging of the tooth, for example, the outer enamel is a very strong reflector and thus, produces a large amplitude echo signal, whereas the interior of the tooth, which it is desired to examine, is a much weaker reflector, and accordingly, produces a very weak return signal, often so small relative to the signal reflected by the enamel which immediately precedes it, that it goes undetected. In accordance with one aspect of the present invention, the gain of the signal processing circuit is adjusted automatically and instantaneously so that the large pulse is not significantly affected whereas substantial gain is applied to the small echo to make it "visible".

As used herein, the term "repeatability" means that the image presented on the display for a given internal organ, or an internal organ affected by a particular disease, should be substantially the same (1) when the same patient is examined at different times so that changes in the diseased portion can be observed, (2) when different patients, having widely different body characteristics, are examined, or (3) the same patient is examined by a different diagnostic equipment at separated geographic locations. More particularly, assuming that an artery is to be examined, in a patient having a lot of fat much of the energy in the transmitted sound pulse is absorbed and/or reflected by the fat with the consequence that the amount of energy available to be reflected by the artery would be much lower than in a patient who has little or no fat. The larger echo signal from the second patient would show up brighter on the display than the weaker signal from the fat patient, even if the condition of the artery were the same in both. If one is interested in only detection this may be a problem, but to enable the physican to train himself to detect a particular disease of an organ, and the extent of it, the display desirably should have one shade of brightness for a healthy organ and a discernibly different shade of brightness for a diseased organ. That is, if the display could be made to have the same brightness for a given internal organ regardless of the body structure of the patient, the disease would automatically show up discernibly less bright than the healthy organ so that the physician could think in these terms and be on the lookout for a particular diseased condition, much in the same way that radiologists have developed the skill of reading x-ray photographs. Thus, "repeatability" means that the displayed image for a given condition for a particular organ should be the same day-to-day for the same patient, or patient-to-patient, or when the organ is examined from different sides, in which case the intervening tissue layers may be and usually are completely different.

Factors interfering with detectability and repeatability in ultrasound imaging are absorption effects in the object medium, and two primary mechanisms of geometrical or radiation damping, namely, damping due to beam spreading (or its inverse effect of increase in intensity due to focussing) and reduction in the incident sound intensity at successive interfaces due to reflection and scatter at the preceding interfaces and/or media.

The nature of the "beam spreading" problem will be seen in FIG. 2, in the lower portion of which is schematically shown a transducer 16, which may be of the kind described in co-pending application Ser. No. 515,353 filed Oct. 16, 1974 in the names of Anant K. Nigam and William E. Glenn, which produces a narrow beam sharply focused at a focal plane 17. As the beam enters the imaging media, it narrows down to a very small area at the focal plane and spreads out again at distances beyond the focal plane. Representing the total power from the transducer as $P = I_1 A_1$ (intensity times the beam cross-section), the intensity of the beam at the plane labeled X (assuming no attenuation between the transducer and the plane X) is higher than the intensity at the transducer, having a value of $I_2 = I_1 A_1 / A_2$. Thus, if a reflecting body were present at plane X, the intensity of the reflected signal would be proportional to $I_2$.

Similarly, at the plane labeled Y, and again assuming no attenuation between the transducer and this plane, the intensity is even higher, having a value of $I_3 = I_1 A_1 A_3$. The intensity is greatest at the focal plane 17, and at distances beyond the focal plane the beam spreads out again with a consequent reduction in ultrasound intensity. Although a focused beam has been shown to illustrate the damping effects of beam spreading (or focussing), the same problem exists with dynamically focused transducers.

Damping due to spreading can be measured experimentally by directing the beam into a homogenous medium, such as a free-standing water bath, and using a small probe at several locations along the axis of the beam the pressure distribution as a function of the distance from the transducer is readily obtained. Because the arrival time, $t$, at the transducer from any given point $z$ on the axis is equal to $2zc$, $p(z) = p(t)/2c$ may be treated as a time-function and can be compensated for electronically as a function of time after pulse initiation. The curve in the upper portion of FIG. 2 shows the axial pressure distribution of a particular transducer based on untrasound velocity $c = 1500 m/sec$. By providing a compensating gain which is proportional to the illustrated curve, the effect of damping due to beam spreading can be compensated. Thus, the signal-processing circuit 22 of the system schematically shown in FIG. 1 includes as its first stage a circuit 30 to which the echo signals from the preamplifier 19 are applied for providing compensation for beam spreading effects. The appropriate time-gain correction may, for example, be stored in conventional digital storage means, such as a read only memory (ROM), to be read out in response to each transmitted pulse for application as a control signal for a voltage controlled amplifier.

The significance of the described correction for beam spreading effects will be evident from examination of FIGS. 2A and 2B. FIG. 2A, lower trace, show a typical A-scan (single line of an image field) of an "object" consisting of five "identical" interfaces with the focus of the transducer at the third interface. The upper trace of FIG. 2A represents the DC control voltage which is applied to a voltage controlled amplifier. FIG. 2B shows the same signal with the compensation for beam spreading disconnected. It is seen from FIG. 2B that the echo strength from the interface depends on how far it is from the focus of the beam where the incident ultrasound intensity is highest. When the described correction is provided it is noted that the echo amplitude is no longer a function of distance of the interface from the transducer, thus insuring repeatability of gray scale regardless of how far from the transducer the object is, as may happen by reason of not having identical positioning of the transducer relative to the patient from one test to the next. Since different equipments have different transducer focussing characteristics, when each equipment is corrected for its own unique "beam spreading" effects, all equipments will then produce the same gray scale so as to insure repeatability from equipment to equipment.

The compensated echo pulses delivered by circuit 30 are next applied to a time-gain compensation circuit 32 which provides compensation for absorption of ultrasound energy in the imaging media. If the body of the patient were homogeneous the wave reflected by an interface in the patient close to the transducer 16 has higher energy than the wave reflected from an interface further removed from the transducer. The TGC unit is used for the purpose of adjusting the gain of the echo signals in accordance with the exponential gain function $e^{+at/c}$. Because different imaging media have known different absorption coefficients, $a$, the TGC unit 32 contains provision for selecting appropriate values of $a$ by a single, operator-controlled knob 32a, or by standard automated means.

In commonly employed ultrasonic imaging setups, the object 18 to be imaged (e.g., the patient, or the part of his body of interest) is immersed in water, shown schematically at 16a, and maintained at a suitable distance from the transducer 16. Since in the range of frequencies employed in diagnostic imaging there is very little absorption in the water path, the time-gain function is initiated only after the first echo, representing the front surface of the body being imaged, is received. To this end, a trigger circuit 34, operative in response to such first echo, generates a trigger pulse for initiating the time-gain function. Since the time-gain compensation unit 32 is otherwise well known in the art, it is believed unnecessary to describe it in further detail.

Turning now to the other of the aforementioned mechanisms of geometrical damping, and with reference to FIG. 3, damping due to reflections results primarily because as the ultrasound propagates across an interface, a portion of it is reflected. As shown in the schematic representation of FIG. 3, the object 40 it is desired to image is separated from the transducer 16 by a first coupling medium (which might be the water coupling path mentioned earlier), two contiguous layers 44 and 46, and a portion of a third layer 48 which surrounds the object 40, which represent three distinct interfaces across which the ultrasound must propagate before reaching the front surface of the object 40. Moreover, the layers 44, 46 and 48 may have different impedances $Z_1$, $Z_2$, and $Z_3$, respectively, and the reflection from each of the interfaces, is in turn, a function of these impedances as well as the incident energy. At each interface, the reflected and transmitted intensities $I_R$ and $I_T$ are algebraically related: $I_T = I_i - I_R$, where $I_i$ is the incident ultrasound intensity. For imaging of subsequent interfaces, therefore, only a smaller portion of the energy $I_i$ is available. More particularly, in the illustrated example, if the pulse from the transducer 16 has an intensity $I_1$, the echo reflected from the front surface of layer 44 has an intensity $I_2$ which is proportional to the impedance $Z_1$ of layer 44 and of the incident intensity $I_1$, leaving an intensity for transmission through layer 46 of $I_1 - I_2$. A portion of this energy, designated $I_3$, is reflected from the interface of layers 44 and 46, and so on, such that the intensity of the ultrasound pulse finally reaching the object 40 is $I_1 - I_2 - I_3 - I_4$. Thus, a single trace A-scan might appear as shown at the bottom of FIG. 3, usually with the largest echo being returned from the interface between the medium 42 and layer 44, the succeeding echoes being progressively diminished, with the echo from the object 40 being so small relative to the others as to be difficult to detect.

An important feature of the present invention is the provision in the signal-processing system 22 of additional gain proportional to $I_i/I_T = I_i/(I_i - I_R)$ subsequent to each reflection, thereby to simulate uniform intensity imaging. This can be accomplished because knowledge of both $I_i$ (the intensity of the pulse going out from the transducer) and $I_R$ (the intensity of each of the successive echo pulses from the successive interfaces) is available at the receiver. Thus, in the general block diagram of FIG. 1, the signal available at the output of the TGC unit 32 is divided into two branches, a control branch 50 including means 52 for accumulating return energy, and a signal branch 54 including a voltage controlled amplifier 56, the gain of which is controlled by a DC control signal produced by the accumulator 52. The signal available at the output of the voltage controlled amplifier 56, now compensated for beam spreading (and its inverse) effects, absorption effects and effects due to decrease in energy because of reflections, is detected by the detector 23 to produce a display signal for application to the display 24.

Referring now to FIG. 4, a preferred circuit for producing the control signal for amplifier 56 includes, in essence, means for producing a DC voltage proportional at any time, $t$, to the total reflected energy received by the transducer 16 up to time $t$. To this end, the received echo pulse appearing at the output terminal of amplifier 56 (two of which are illustrated) is squared in a suitable squaring circuit 60 and integrated over the period of the pulse by an integrating circuit 62 thereby to develop a signal proportional to the average total energy of the pulse. Assuming that the first pulse $I_2$ is the pulse reflected from the first interface in FIG. 3, the DC signal at the output of integrator 62 has a value proportional to the square of the area under the pulse $I_2$. The level of this signal is stored in a cumulative hold circuit 64, which may include a storage capacitor. This stored level at any instant of time is proportional to the total energy of the echoes received up to that time following pulse initiation; that is, it is proportional to $I_R$ which equals the sum of $I, I_2, I_3 \ldots I_n$ received up to that time. It is to be noted that a correction of the form $I/(I-I_R)$ may be complicated to implement insofar as it requires that the echo signals be electrically subtracted from a fixed level (I) to obtain an electrical signal proportional to $(I-I_R)$ and the fixed level (I) electrically divided by the latter signal to achieve $I/(I-I_R)$. The circuit of FIG. 4 achieves a simpler implementation by using the approximation $$\frac{I}{I - I_R} = (\frac{1 - I_R}{I})^{-1}$$

$$= 1 + (\frac{I_R}{I})^2 + (\frac{I_R}{I})^3$$

$$\approx 1 + \frac{I_R}{I}$$

A signal proportional to this approximate function, containing first or higher order terms as appropriate, is applied to the voltage controlled amplifier 56 to vary its gain by a proportional amount. Upon occurrence of the next pulse the cumulative hold circuit 64 automatically adjusts to the new level established by the additional pulse $I_3$, and the process is repeated for each successively received echo pulse following the main bang from the transducer. The change in gain becomes effective after the pulse causing the change has passed; that is, the change in gain caused by a particular pulse is applied only to all the next subsequent pulses. The change in gain from pulse-to-pulse thus is interactive, automatically correcting for all of the reflections from interfaces across which the ultrasound propagates, thereby to cause the system to perform as if the beam were of essentially uniform intensity at all levels of penetration. Accordingly, whether the patient has a lot or a little of acoustically reflecting tissue between the transducer and the internal organ it is desired to examine, the echo returned from the internal organ has essentially the same amplitude and thus produces the same degree of brightness on the display 24, thereby effectively solving the problem of repeatability in ultrasound imaging. The cumulative hold circuit 64 is discharged prior to initiation of each transmitted pulse by application of a trigger pulse from timing circuit 10.

While the system of FIG. 4 has been described as producing the control signal for the amplifier 56 by squaring and intergrating the pulses appearing at the output terminal of the amplifier, thus insuring that the change in gain will not be applied until after the pulse which caused the change has passed, it is to be understood that, alternatively, the input pulses to amplifier 56 may be squared and integrated to generate the control signal for the amplifier. Inasmuch as the echo pulses have a duration of the order of one microsecond, the squaring and integrating circuits 60 and 62 can be made to have sufficient inherent delay that the change in the control voltage caused by a given pulse does not become effective until after that pulse has passed the amplifier.

The described interactive gain compensation also contributes significantly to the detectability of echoes, as will be seen from an examination from FIGS. 5 and 6. FIG. 5 is a reproduction of a photograph of oscilloscope traces, the lower being a typical A-scan, (single line of the image field), made with the reflection compensation circuitry of FIG. 4 in operation, and the upper trace representing the DC control voltage (which in the system of FIG. 4 is inversely proportional to the gain) applied to amplifier 56, and FIG. 6 shows the same signal with the interactively generated DC correction signal disconnected from the amplifier. Referring first to FIG. 5, the first received pulse is not subjected to much gain, but through the action of the IGC circuit, pulse 1 caused the gain to increase before the arrival of pulse 2, thereby enhancing pulse 2. Pulse 2, in turn, caused a further increase in gain to thereby bring up the level of the next successive pulse 3 and so on, the effect of the interactive correction being to make detectible very weak echo pulses. A comparison of the amplitudes of the corresponding pulses in the A-scan traces of FIGS. 5 and 6 dramatically illustrates the effectiveness of the interactive gain correction. Not only is the amplitude of all of the echo pulses in FIG. 6 reduced, but pulses 5, 6 and 7, small pulses which follow a relatively larger amplitude pulse 4, did not even appear on the trace, and the last to arrive pulses (those appearing toward the right on the FIG. 5 trace) were not detected.

It will be evident from the foregoing that the described gain compensation system effectively compensates for the major causes of image degradations in pulse-echo imaging systems. Since it corrects for the major attenuation mechanisms associated with "beam spreading" and reflections, there is no longer any need to make the TGC flexible (and complicated), and essentially a single knob 32a for selecting the average value of $\alpha$ need be provided to give full compensation for absorption effects as dictated by Eq. 1, thus greatly simplifying the operation of the equipment. Further, the IGC makes possible similar quantitative images of similar imaging volumes, such as for example, the same internal organs of two different patients. A very significant advantage of the system is that it makes possible the imgaing of heretofore "impossible" structures such as the tooth. The tooth is a complex structure in which the front surface (enamel) reflects more than 90% of the incident ultrasound energy, and the echoes from the succeeding interfaces which arrive only a few microseconds later, are almost 30db lower. Because the tooth could be located almost anywhere inside the cheek of the patient, it would be next to impossible without the use of the described IGC system, to satisfactorily image the dental structure. A similar case can be made in the repeatable imaging of artery wall strata, bone marrow, gall stones, etc., as well as cracks, fissures and other flaws in materials during non-destructive testing by pulse-echo ultrasound apparatus.

I claim:

1. In ultrasonic pulse-echo apparatus of the type including a transducer for directing a beam of ultrasound pulses toward a multilayered object to be examined and for converting ultrasound echo pulses reflected from interfaces between the layers within the object into electrical pulses, and television-type display means responsive to the electrical pulses for displaying the image of said object, the improvement comprising:
   signal processing means connected between said transducer and said display means for varying the gain of said electrical pulses and coupling the pulses to said display means, said signal-processing means including
   first means responsive to said electrical signals for varying the gain interactively to provide a gain value which at any instant of time following transmission of each ultrasound pulse from the transducer is substantially proportional to the cumulative energies of the echo pulses received by the transducer up to said instant of time for providing corrections for attenuation of the ultrasound beam due to reflections within said object.

2. Apparatus according to claim 1, wherein said signal-processing means further includes
   second means for varying the gain of said electrical pulses in accordance with a first predetermined time-gain function for providing corrections for spreading and/or focussing of the ultrasound beam.

3. Apparatus according to claim 1, wherein said signal-processing means includes
   further means for varying the gain in accordance with a second predetermined time-gain function for providing correction for effects of absorption of the ultrasound beam in said object.

4. Apparatus according to claim 2, wherein said signal-processing means further includes
   third means for varying the gain in accordance with a second predetermined time-gain function for providing correction for effects of absorption of the ultrasound beam in said object.

5. Apparatus according to claim 2, wherein said first predetermined time-gain function of said second gain-varying means is shaped to provide on-line correction for spreading and/or focussing effects of the ultrasound beam so as to simulate uniform ultrasound intensity distribution throughout the axial path of said beam.

6. Apparatus according to claim 1, wherein said first gain-varying means comprises
   voltage-controlled amplifier means to which said electrical pulses are applied,
   means for integrating said electrical pulses as a function of time for developing a control signal having an amplitude proportional at any time $t$ to the cumulative energies of the echo pulses received by the transducer up to said time $t$, and
   means for applying said control signal to said voltage-controlled amplifier means for controlling the gain thereof in real-time.

7. Apparatus according to claim 6, wherein said first gain-varying means further comprises
   means for storing the cumulative energies of the echo pulses received by the transducer, and
   means responsive to the transmission of each ultrasound pulse from the transducer for discharging said storing means.

8. Apparatus according to claim 3, wherein said further gain-varying means includes operator-controllable means for selecting said second predetermined time-gain function in accordance with the absorption coefficient of the object to be examined.

9. Apparatus according to claim 1 further comprising
   means to detect the output from said signal-processing means for deriving out an image signal for application to said display means.

10. Apparatus according to claim 1, wherein said first gain-varying means comprises:
    voltage-controlled amplifier means for receiving and amplifying the output signal from said transducer,
    means connected to receive the output from said amplifier means for integrating said electrical pulses as a function of time for developing a control voltage the amplitude of which at any time $t$ following transmission of each pulse by the transducer is proportional to the cumulative energies of the echo pulses received by the transducer up to said time $t$,
    means for storing the cumulative energies of the echo pulses received by the transducer,
    means for applying said control voltage to said voltage controlled amplifier means for controlling the gain thereof in real-time, and
    means responsive to the transmission of each ultrasound pulse from the transducer for discharging said storing means.

11. Apparatus according to claim 10, wherein said signal-processing means further includes
    second means for varying the gain of said electrical pulses in accordance with a first predetermined time-gain function shaped to provide on-line correction for spreading and/or focussing effects of the ultrasound beam produced by said transducer so as to simulate uniform ultrasound intensity distribution throughout the axial path of said beam.

12. Apparatus according to claim 11, wherein said signal-processing means further includes
    third means for varying the gain in accordance with a second predetermined time-gain function which is proportional to the absorption coefficient of the object to be examined, and
    wherein said third gain-varying means includes means for selecting according to absorption coefficient the appropriate time-gain function for the object to be examined.

13. Apparatus according to claim 12, wherein said means for selecting the appropriate time-gain function is operator-controllable.

14. In an ultrasonic pulse-echo apparatus of the type including a transducer for directing a beam of ultrasound toward a multilayered object to be examined and for converting ultrasound echo pulses reflected from interfaces between the layers within the object into electrical pulses, and display means responsive to the electrical pulses for displaying an image of the object, an improvement comprising:
    amplifier means, responsive to a gain control signal, for coupling said electrical pulses to said display means; and
    gain control means for generating a gain control signal which depends on the cumulative energies of the echo pulses received by said apparatus.

* * * * *